United States Patent [19]
Knutson

[11] Patent Number: 5,803,734
[45] Date of Patent: Sep. 8, 1998

[54] DENTAL DAM SUPPORT AND METHOD OF USE

[76] Inventor: Eric J. Knutson, 11443 Hesperian Cir., Gold River, Calif. 95670

[21] Appl. No.: 773,266

[22] Filed: Dec. 23, 1996

[51] Int. Cl.$^6$ ................................ A61C 5/14; A61C 5/12
[52] U.S. Cl. ............................................ 433/136; 433/139
[58] Field of Search ............................ 433/48, 136, 137, 433/138, 139

[56] References Cited

U.S. PATENT DOCUMENTS

| | | |
|---|---|---|
| 562,490 | 3/1896 | Richter . |
| 722,033 | 2/1903 | McCarter . |
| 1,010,146 | 11/1911 | Ivory . |
| 3,772,790 | 11/1973 | Swan-Gett et al. ...................... 433/136 |
| 4,214,870 | 7/1980 | Fagelman .................................. 433/40 |
| 4,986,752 | 1/1991 | Graves ..................................... 433/138 |
| 5,011,407 | 4/1991 | Pelerin ...................................... 433/48 |
| 5,066,231 | 11/1991 | Oxman ..................................... 433/214 |
| 5,104,317 | 4/1992 | Riazi ........................................ 433/136 |
| 5,112,225 | 5/1992 | Diesso ....................................... 433/48 |
| 5,213,498 | 5/1993 | Pelerin ....................................... 433/37 |
| 5,503,552 | 4/1996 | Diesso ....................................... 433/37 |

OTHER PUBLICATIONS

R. G. Graves, Cushee System™ Brochure, 1988, Pacific Rim Dental Innovations Ltd., Hillside Printing, Victoria B C Canada.

H. Wakabayashi, et al., A Clinical Technique for the Retention of a Rubber Dam Clamp, Journal of Endodontics, vol. 12, No. 9, Sep. 1986, pp. 422–424.

I.W.M. Jeffrey & M.J. Woolford, An Investigation of Possible Iatrogenic Damage Caused By Metal Rubber Dam Clamps, Int'l Endodontic Journal, vol. 22, No., 2, Mar. 1989, (pp. 85–91) p. 91.

William H. Liebenberg, An Innovative Method of Cushioning Metal Clamp Jaws During Rubber Dam Isolation, Journal Canadian Dental Assn., vol. 61, No. 10, Oct. 1995, pp. 878–880.

William H. Liebenberg, Posterior Composite Restorations: Operative Innorations, Practical Periodontics and Aesthetic Dentistry, vol. 8, No. 8, Oct. 1996, p. 769.

William H. Liebenberg, Rubber Dam Isolation of Cervical Lesions, FDI World, vol. 3, No. 5, Sep.–Oct. 1994, pp. 18–24.

R. Garry Graves, The Rubber Dam Clamp Cushion, Oral Health, Dec. 1989, vol. 79, No. 12, pp. 47, 48.

*Primary Examiner*—Cary E. O'Connor

[57] ABSTRACT

The dental dam support (10) and donut (16) are comprised of a moldable, hardenable material for use as a support means for a dental clamp (14), which can prevent clamp (14) from contacting the teeth or gingiva, during anchorage of a dental dam (18). The material achieves sufficient hardness to support clamp (14) over gingiva alone, if the tooth structure is insufficient, enhances the stability of clamp (14) on the tooth or gingiva, and inhibits fluid movement past clamp (14). Softened support (10) or donut (16) material is molded over the teeth or gingiva to be clamped, clamp (14) is partly seated into the material and restrained while the material is hardened. Clamp (14) is released such that it engages the support material. Another use of support (10) is to anchor dam (18) without clamp (14). Softened support (10) is molded over teeth where anchorage is desired. Support (10) is hardened and removed from the teeth. Dam (18) is placed over the teeth, and support (10) is replaced over dam (18), thereby anchoring dam (18) to the teeth. Another use of donut (16) is to isolate an area of a tooth. Softened donut (16) is molded to cover a perimeter area about an exposed work area on the teeth, and hardened.

24 Claims, 3 Drawing Sheets

DENTAL DAM SUPPORT AND METHOD OF USE

BACKGROUND

1. Field of Invention

This invention relates to dentistry, specifically to dental dam anchoring and support.

2. Description of Prior Art

Dental dams are utilized in dentistry to isolate specific areas of the mouth. Dental dams inhibit the movement of matter to and from the isolated area. They are comprised of a sheet of material, which is typically elastic, such as latex. Methods have been devised to anchor and position dental dams. These include dental clamps, cushions for dental clamps, wires, hardenable compounds, elastic anchors, tie-down strands, wedges, and so on.

Dental clamps are devices which anchor dental dams by engaging a tooth, including any dental restorations comprising the tooth. Dental clamps also commonly engage gingiva (gums) somewhat, although usually inadvertently. Sometimes dental clamps must substantially engage gingiva, such as when supporting tooth structure is compromised, or an extensive restorative procedure is planned. The clamp features opposing jaws for engaging the tooth, gingiva, or tooth and gingiva, hereinafter referred to as the tooth or gingiva, with sufficient force to resist dislodgment. A biasing means connects between the jaws of many dental clamps, to bias the jaws towards each other. As such, the biasing means provides the force required to securely engage the tooth or gingiva.

The force of the jaws applied to the tooth or gingiva is commonly sufficient to damage the tooth or gingiva. Subsequently, the patient can experience pain, bleeding, bacteremia, a need for anesthesia may need to be administered, and other sequelae from compromising the gingival mucosa. The tooth or gingiva can require repair. The tooth, especially the cementum, can become sensitized. Alternatively, the clinician may elect to dispense with use of a dental dam, with the problems inherent therein. Consequently, there is a need to disperse the forces of the clamp so that such trauma is reduced.

In addition, the clamp jaws sometimes cannot securely engage the tooth or gingiva sufficiently to prevent dislodgment. This is most commonly occurs when a tooth has insufficient undercut structure for the jaws to engage. When accidental dislodgment of the clamp occurs, much time may be lost for the clinical procedure, and the patient may experience other trauma, including aspiration of objects. Consequently, there is a need to improve the security of the engagement.

Further, when the clamp secures an isolation dam, the clamp can partially defeat the isolation by permitting fluids to flow by the clamp. Consequently, there is a need to improve the sealing about the clamp.

U.S. Pat. No. 562,490 to Richter discloses a rubber dam clamp consisting of a flexible wire arrangement on metallic dental clamps employed to hold or retain absorbent wadding rolls. The metal of the clamp touches the tooth.

U.S. Pat. No. 722,033 to McCarter discloses a dental clamp in which the jaws of the clamp grip firmly the opposite sides of the tooth to be treated. It would appear that this device has the metal of the clamp in direct contact with the tooth.

U.S. Pat. No. 1,010,146 to Ivory discloses a pad holder for dental purposes. This device consists of means for holding an absorbent pad on the gingiva during a dental operation so as to absorb saliva at or about the tooth. The pad appears to be interposed between the tooth or gingiva, and jaws of the clamp, thus possibly protecting the tooth from the jaws to some extent. In some of the figures of the patent, however, the metal of the clamp appears to contact the teeth. The patent describes the pads fitted over the teeth and held firmly on the gingiva. Because the patent utilizes an absorbent pad, which is necessarily porous, it does not provide effective sealing. Moreover, the pads do not grip the clamp in such a manner as to be likely to prevent slipping.

U.S. Pat. No. 4,214,870 to Fagelman discloses a dental clamp for maintaining pressure on a matrix strip to insert restorations on a tooth. Absorbent wadding rolls are interposed between the clamp and tooth. This clamp is not specified for use in retaining a dental dam.

U.S. Pat. No. 4,986,752 to Graves discloses an elastomeric dental clamp cushion, and method of securing a dental clamp. The molded cushion features a slot recess on one side, which is fitted over the entire tooth contacting edges of the clamp jaws. Tooth engaging ridges are on the opposite side. The clamp, with at least one cushion, is placed on a tooth, such that a portion of the cushion is interposed between the contact edge of the clamp and the tooth, and the tooth engaging ridges are in contact with the tooth. Disadvantages include preclusion of use on teeth with a low height of contour, or on teeth requiring restorations with deep buccal or lingual extensions from the cavity preparation, because the cushion may be in the clinician's way. Additional disadvantages include the need to stock a selection of sizes of cushions to fit different types of dental clamps, cushions are easily lost due to the small size, and cushions are easily dislodged from the clamps.

Cushee System™ brochure, Pacific Rim Dental Innovations, Victoria, BC, Canada, 1988, discloses further disadvantages of the clamp cushion of U.S. Pat. No. 4,986,752, the disadvantages being that the cushion may impinge on the gingiva when used on teeth with deep cervical abrasion, and that the sharp points on some types of dental clamps should be ground down.

U.S. Pat. No. 5,112,225 discloses a method for making a custom dental tray, such as for holding impression material, with a thermosetting material, such as polycaprolactone. The thermosetting material is not specified for use with dental clamps or dental dams.

U.S. Pat. No. 5,213,498 to Pelerin discloses a method for making a custom impression tray with a thermosetting material, such as polycaprolactone. The thermnosetting material is not specified for use with dental clamps or dental dams.

Hajime Wakabayashi, et. al., *A Clinica Techniqhue for the Retention of a Rubber Dam Clamp*, Journal of Endodontics, Vol. 12, No. 9, September 1986, discloses a method of cushioning dental clamps employing flowable self-curing resin material. The resin is applied in a thin layer, and cured on the dried tooth surface upon which the clamp is anticipated to rest.

I. W. M. Jeffrey & M. J. Woolford, *An Investigation of Possible Iatrogenic Damage Caused By Metal Rubber Dam Clamps*, International Endodontic Journal, Vol. 22, No. 2, March 1989, discloses the use of a cushioning coating for the inner margins of dental clamps.

William H. Liebenberg, *An Innovative Method of Cushioning Metal Clamp Jaws During Rubber Dam Isolation*, Journal Canadian Dental Association, Vol. 61, No. 10, October 1995, discloses a method of cushioning dental clamps employing flexible, visible light-curable temporary dental materials. Fermit-N (IVOCLAR NORTH AMERICA, INC.) is preferred, but also listed as practical alternatives are E-Z Temp (COSMODENT), Intertemp (E&D DENTAL PRODUCTS, INC.), Tempo-Rex (SCI PHARM), Triad VLC Provisional Material (DENTSPLY), Barricade (L. D. CAULK), and LC Blockout Resin (ULTRADENT PRODUCTS, INC.). Acrylic and composite restorative resin dental materials are described as too brittle, and too tedious to remove from interproximal areas for use in the method.

The cushion placement method involves introducing the cushioning material into both mesial and distal interproximal embrasures of the clamp anchor tooth. The material is hardened by light exposure. The clamp is seated, such that the contacting edge of the jaws rests on the hardened material. Disadvantages include the failure to establish a fluid seal between the clamp and the tooth, and limitation of use only for areas where interproximal embrasures are present to secure the cushion material. In addition, the cushioning material is costly.

Hard wax compounds, such as Green Stick Compound (BUFFALO DENTAL), can enhance the stability of dental clamps. Such compounds are softened and applied to the clamps and the teeth, which are bound together upon hardening of the compound. This inhibits slippage of the clamp along the tooth surfaces. However, such compounds are not specified to prevent contact of the clamp with the tooth or gingiva. These compounds can also bind a dental dam to the teeth alone, without concurrent use of a clamp, such as for a slit-dam, general field isolation of multiple teeth. However, the compound is somewhat inconvenient to use, and must be fractured to remove from the teeth and dental dam.

William H. Liebenberg, *Posterior Composite Restorations: Operative Innovations*, Practical Periodontics and Aesthetic Dentistry, Vol. 8, No. 8, October 1996, discloses a method of stabilizing dental clamps employing flexible, colored, visible light-curable resins to stabilize dental clamps. Such materials include Blue Block-out (ULTRADENT PRODUCTS, INC.) and Green Nite White (DISCUS DENTAL). The clamp is seated on the tooth. The cervical enamel is acid etched to provide micromechanical retention of the resin. The resin is applied occlusal to the clamp, and hardened by light exposure. Following removal of the dental dam, the resin is scraped and polished from the teeth.

Blue Block-out (ULTRADENT PRODUCTS, INC.) and Green Nite White (DISCUS DENTAL), and similar resins, are also used to provide isolation of tooth surface areas. Such isolation is more precise than a dental dam is capable of providing, although a dental dam may be used concurrently to provide more general over the remaining portions of the mouth. Such isolation enhances protection of the exposed work surface area from oral fluids, and enhances protection of the covered tooth or gingiva surfaces from procedures, such as chemical or mechanical etching. At the conclusion of the dental procedure, the resin is scraped and polished from the teeth.

William H. Liebenberg, *Rubber Dam Isolation of Cervical Lesions*, FDI World, Vol. 3, No 5, September–October 1994, discloses methods of adhering dental dam material to gingiva. One such method employs adhesive intraoral contact strips used in electronic dental anesthesia. Another such method employs cyanoacrylate glue applied directly to the gingiva immediately followed by pressing the dental dam material onto the glue coated gingiva.

U.S. Pat. No. 5,104,317 to Hygienic Corp. discloses cylindrical elastic material for anchoring dental dams. A segments of the elastic material is wedged interproximally to prevent the dental dam from slipping up through the contact area between adjacent teeth. Segments are effective when adjacent teeth are in close proximity to one another, and the holes for the teeth in the dental dam are small. However, when the teeth are not in close proximity to one another, the segment cannot be securely wedged between the teeth. Similarly, when the dental dam tooth hole is too large, the dam tends to slip over the segment.

Dental wedges and orthodontic separators are used similarly to these elastic material segments, and suffer from similar disadvantages. Tie down strands, such as dental floss or wire, cinch around the dental dam and tooth simultaneously, to anchor the dam. However, these tend to work down toward the gingiva, loosening the tie-down, such that the dam tends to slip out from under the grasp of the strand.

The above dental dam supports suffer from a number of disadvantages:

(a) Supports are stabilized primarily by contact with teeth.
(b) Supports require a clamp which fits the anchor tooth.
(c) No support can maintain a dental dam fluid seal when anchored by a tooth with low height of contour.
(d) No support can maintain a dental dam fluid seal without interfering with deep buccal or lingual cavity preparation extensions.
(e) No support can maintain a dental dam fluid seal when anchored by a tooth with deep cervical abrasion, without impinging on the gingiva.
(f) No moldable support can anchor a dental dam, being capable of rapid, intact removal.
(g) No moldable support can isolate a surface area of a tooth, being capable of rapid, intact removal.

A device similar to my dental dam support is not already in use primarily because related dental dam supporting has been a somewhat obscure practice to date. It remains obscure because dam supporting of the art provides only partial supporting, and is inconvenient. The recent progress of dentistry to increasingly provide procedures that do not require complete anesthesia will increase the demand for dental dam use that is atraumatic and convenient.

OBJECTS AND ADVANTAGES

Accordingly, several objects and advantages of my invention are:

(a) to provide a dam support which adequately stabilizes a dental clamp mounted on gingiva only;
(b) to provide a dam support which adequately supports dental clamps independent of the tooth or clamp shape;
(c) to provide a dam support which can substantially maintain a dental dam fluid seal when mounted with a dental clamp on teeth with low height of contour;
(d) to provide a dam support which can substantially maintain a dental dam fluid seal when mounted with a dental clamp, without interfering with deep buccal or lingual cavity preparation extensions;
(e) to provide a dam support which can substantially maintain a dental dam fluid seal when mounted with a dental clamp on teeth with deep cervical abrasion, without impinging on the gingiva.
(f) to provide a moldable dam support which can substantially anchor a dental dam, being capable of rapid, intact removal.

(g) to provide a moldable dam support which can substantially isolate an area of tooth surface, being capable of rapid, intact removal.

Further objects and advantages are to provide a clamp support which is economical, and which may be employed without interproximal embrasures mesial and distal to the clamped tooth. Still further objects and advantages will become apparent from a consideration of the ensuing description and drawings.

DRAWING FIGURES

Figure 1:
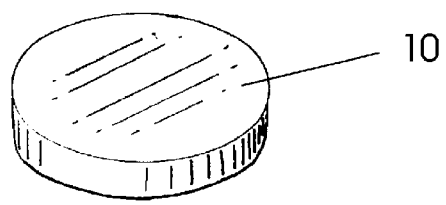
FIG. 1 shows a perspective view of a dental dam support.

| Reference Numerals in Drawings | |
|---|---|
| 10 support | 12 adhesive |
| 14 clamp | 16 donut |
| 18 dam | |

DESCRIPTION—FIGS. 1 TO 6

According to one aspect, the invention provides a method for supporting a dental clamp having opposing jaw members for engaging oral structures, such as teeth and gingiva, the jaw members biasable toward each other, the method comprising the steps of: introducing a pliable mass hardenable dental material onto portions of the teeth, portions of the gingiva, or portions of the teeth and gingiva; molding the hardenable dental material to form a support of hardenable dental material; restrainingly seating the jaw members of the dental clamp partly into the support of hardenable dental material, such that the jaw members imprint, but do not completely penetrate, the support of hardenable dental material, to form an imprinted support of hardenable dental material; substantially hardening the imprinted support of hardenable dental material to form an imprinted support of substantially hardened dental material; and nonrestrainingly seating the jaw members onto the imprinted support of substantially hardened dental material, such that jaw members are biased toward each other.

According to another aspect, the invention provides a dental dam support, support 10, comprising a moldable material which exhibits substantial toughness when hardened. A perspective view of a typical embodiment of support 10 is shown in FIG. 1. The material of hardened support 10 has sufficient toughness to support the substantial pressure exerted upon it by a dental clamp, without permitting the clamp to completely penetrate support 10, or to traumatize oral structures under support 10. As such, hardened support 10 has sufficient toughness to support a dental clamp when it is over gingiva only, rather than requiring placement over teeth. In addition, hardened support 10, without clamp 14, has sufficient strength and stiffness to resist inadvertent dislodgment when placed over the teeth. Further, hardened support 10 has sufficient elasticity and flexibility. As such, support 10 may be rapidly lifted intact out of undercut areas about the teeth, without fracture, remaining immediately resusable.

It is preferred that support 10 be comprised of a thermoplastic, or thermosetting, material that melts or softens to a state of pliability at a temperature less than 65° C., and is solid at 38° C. Representative thermosetting materials include polyesters, polyurethanes, and ethylene vinyl acetate copolymers. The preferred material for support 10 is polycaprolactone, such as a homopolymer or copolymer of epsilon-caprolactone. Such a polycaprolactone optionally can contain property-modifying or crosslinkable functional groups if desired. Blends of polycaprolactones can also be employed. The material is softenable until pliable by heating, such as in a water bath. An increase in transparency that typically occurs at the melting point will provide a convenient indicator of sufficient heating. The softened, pliable material is hardenable by cooling, such as with an air and water spray. It is supplied as a thin disc, or wafer, for heating convenience. The preferred volume of material for individual wafers is approximately 350 $mm^3$, and storage is at room temperature.

However, other materials are effective. For example, some chemically cured, or light-cured, materials, such as some acrylics, exhibit sufficient toughness and elasticity. Temporary composite dental materials currently lack sufficient toughness to support a dental clamp over gingiva alone, without backing support from the teeth, and are costly.

Figure 2:
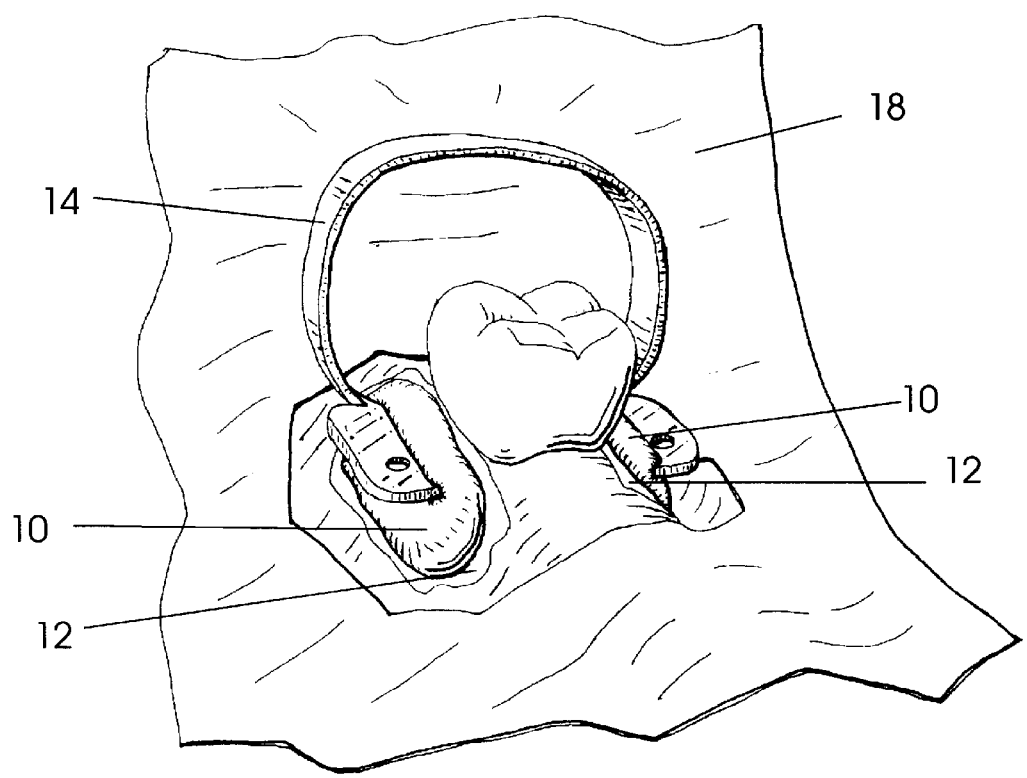
FIG. 2 shows a perspective view of a dental dam support supporting a dental clamp on the gingiva.

FIG. 2 shows a perspective view of a molded support 10 supporting a dental clamp, clamp 14, on the gingiva. In this view, support 10 material has been molded to support clamp 14 on the buccal and lingual gingiva. Clamp 14 is imprinted into support 10, so as to facilitate fluid sealing, and inhibit fluid flow. Adhesive 12 is interposed between support 10 and the gingiva and teeth. A dental dam of the art, dam 18, shown cutaway to reveal support 10 and adhesive 12. Dam 18 otherwise rests against the buccal and lingual surfaces of support 10, immediately under the flat jaws of clamp 14.

Adhesive 12 is an oral adhesive. Adhesive 12 adheres the mass of support 10 material to oral structures, such as during placement and removal of a dental clamp. As such, it resists forces which tend to displace support 10, or which may cause it to fall to the posterior oral cavity.

The preferred material for adhesive 12 is a water based acrylic emulsion, Hydrobond™ (FACTOR II). However, other materials are effective, such as cyanoacrylates.

Figure 3:
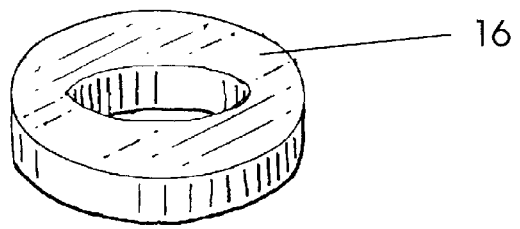
FIG. 3 shows a perspective view of a dental dam support donut.

The invention provides a variant dental dam support, donut 16, comprising a moldable material which exhibits properties that are similar to the properties of support 10. A perspective view of a typical embodiment of donut 16 is shown in FIG. 3. Donut 16 is similar to support 10, but with a central cutout area, or hole. The hole facilitates substantial exclusion of supporting donut 16 material from specific areas, such as the occlusal surfaces of a tooth. It is preferred that the central hole of donut 16 be oval in shape, but any shape is effective. It is also preferred that the hole be of such size and position that no dimension of hardened donut 16 material is less than 2 mm. Donut 16 is fabricated with thin layer of material comprising the outer surface, to enhance handling when softened. Suitable surface materials include friable paper gauze, which tears readily to facilitate molding of donut 16; a fine, loose, stretchable fabric mesh; or a layer of small particles of an inert material concentrated at the donut material surface.

Figure 4:
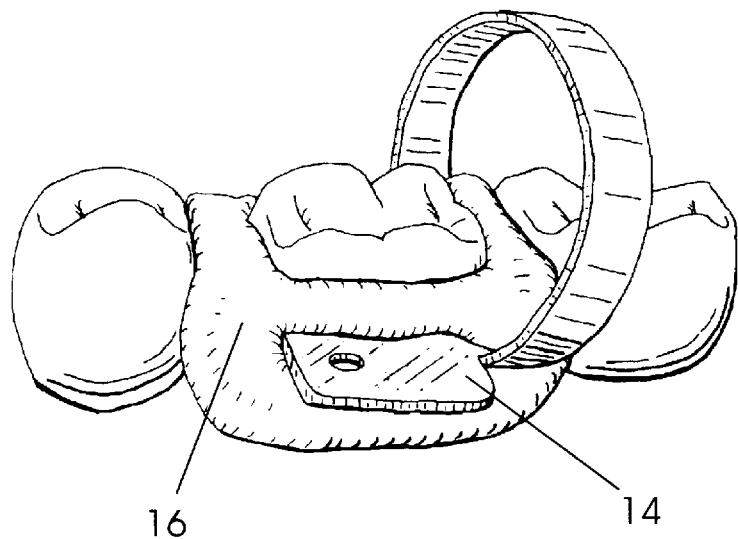
FIG. 4 shows a perspective view of a dental dam support donut supporting a dental clamp over a FIG. 5 shows a perspective view of a dental dam support anchoring a dental dam on the teeth.

FIG. 4 shows a perspective view of a molded donut 16 supporting clamp 14 over a tooth. Donut 16 material is substantially excluded from the occlusal surfaces of the tooth. The material connecting the buccal and lingual/palatal portions is pressed into, the interproximal embrasures spaces. However, donut 16 can support clamp 14 over gingiva alone, similar to support 10. Clamp 14 is imprinted into donut 16 so as to facilitate a fluid seal with clamp 14, donut 16, and the tooth or gingiva.

Figure 5:
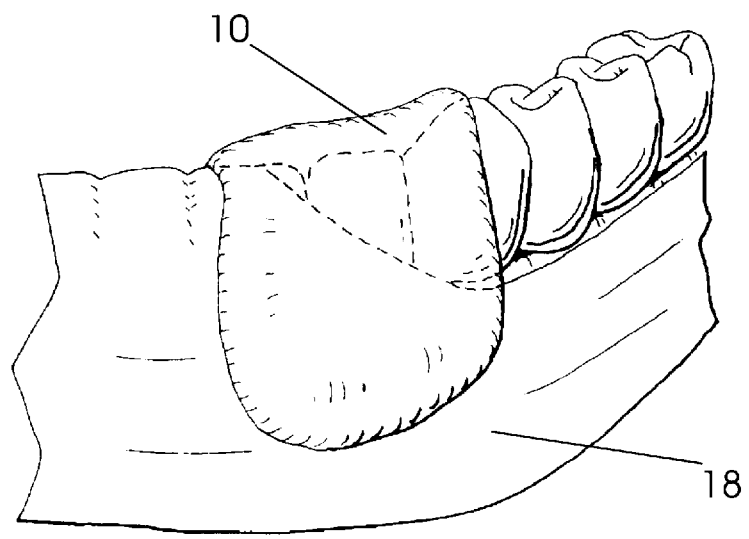

FIG. 5 shows a perspective view of a support 10 on the teeth and gingiva, anchoring dam 18 without clamp 14. Dam 18 is interposed under support 10, and over the teeth and gingiva. Facial and lingual extensions of support 10 position and contour dam 18. Support 10 is rapidly removable and reusable, without fracture.

Figure 6:
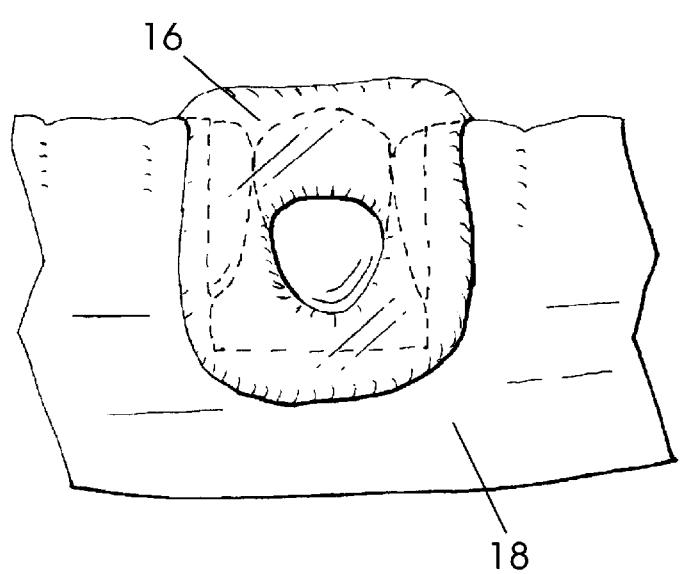
FIG. 6 shows a perspective view of a dental dam support donut isolating an area of tooth surface, and anchoring a dental dam on the teeth.

FIG. 6 shows a perspective view of donut 16 isolating an area of tooth surface, and anchoring dam 18 on the teeth without clamp 14. Dam 18 is interposed under donut 16, and over the teeth and gingiva. Donut 16 is rapidly removable and reusable, without fracture.

From the description above, a number of advantages of my clamp and support become evident:

(a) Support 10 and donut 16 adequately support and stabilize clamp 14 when mounted over gingiva only.

(b) Support 10 and donut 16 adequately support and stabilize clamp 14 independent of the tooth shape, or of the clamp 14 shape.

(c) Support 10 and donut 16, while supporting clamp 14 on teeth which have a low height of contour, can facilitate a fluid seal with dam 18.

(d) Support 10 and donut 16, while supporting clamp 14, can facilitate a fluid seal with dam 18 without interfering with deep buccal or lingual cavity preparation extensions on the mounting tooth.

(e) Support 10 and donut 16, while facilitating a fluid seal with dam 18, can support clamp 14 on teeth with deep cervical abrasion without impinging on the gingiva.

(f) Support 10 can provide substantial anchorage for dam 18, with clamp 14, or without clamp 14, and is capable of rapid, intact removal from the teeth.

(g) Donut 16 can substantially isolate an area of tooth surface, being capable of rapid, intact removal.

Operation—FIGS. 1, 2, 3

By using the dam support of the invention, it is now possible, surprisingly, to atraumatically support and anchor a dental dam clamp on a dental arch without interfering with the teeth. The device offers the advantage that the dental practicioner can now achieve dental dam isolation and fluid sealing around teeth with low height of contour, or with deep cervical lesions, as well as on any other tooth, without trauma to the teeth or gingiva. The need for anesthesia is greatly reduced. In addition, the dam support can be molded to anchor a dental dam to the teeth, without concurrent use of a dental clamp.

Implementation with the device begins with assessing whether clamp 14, support 10, or donut 16 is most effective to anchor and support dam 18. If clamp 14 is preferred, an appropriate clamp 14 is selected. An appropriate clamp 14 is one which most closely fits the cervical contours of the anchor tooth, as this will enhance stability and fluid sealing capabilities. However, it is not necessary that clamp 14 precisely fit the anchor tooth. Neither is it necessary to alter the tooth engaging jaws of clamp 14 to enhance the fit. Support 10 or donut 16 are both capable of supporting variously shaped clamp 14's on variously shaped anchor teeth, with substantial stability and fluid sealing. The tooth engaging jaws of clamp 14 are engaged and expanded with the dental clamp forcep, and the forcep is locked in this position.

A further assessment is made as to whether support 10, or donut 16, is most effective to support clamp 14. If support 10 is preferred, one or more support 10 wafers are softened to a point of pliability. In the preferred embodiment, support 10 is softened by immersion in a 60° C. (140° F.) heated bath containing a suitable inert liquid, such as water or a fluorochemical fluid. Support 10 can also be softened using heat sources such as a hot air gun, hot plate, conventional oven, infrared heater, or microwave oven. After several minutes, an increase in transparency that typically occurs at the melting point will provide a convenient indicator of sufficient heating. Softened support 10 is removed from the bath, and partly dried, such as by using an air stream.

The teeth or gingiva, which are to be covered with support 10, and to which clamp 14 is to be applied, are dried, such as by using an air stream. Adhesive 12 is applied to the dried teeth or gingiva, such as by using an applicator brush, and is slightly dried until tacky, such as by using an air stream.

Softened support 10 is gently pressed onto the adhesive coated teeth or gingiva. Support 10 is manually molded, such that the material of support 10 forms a pad approximately 2 mm in thickness over the area which will support the jaws of clamp 14. Support 10 is partly hardened, such as by partly cooling with a water spray until the material begins to stiffen slightly, and partly regain opacity.

Clamp 14, locked in an expansion by the dental clamp forcep, is introduced by positioning it immediately over support 10. The clamp forcep expansion is slowly released until clamp 14 jaw members are substantially imprinted into the thickness of support 10, but do not completely penetrate through support 10. The dental clamp forcep must continue to restrain the bias force of clamp 14 jaw members toward one another, to prevent such complete penetration of support 10. However, clamp 14 is to be imprinted sufficiently into support 10 to effect a fluid seal between the jaw members of clamp 14 and support 10.

While clamp 14 is thus restrainingly held, support 10 is completely hardened, such as by further cooling with water spray. Clamp 14 is released from the dental clamp forcep. As such, the biasing force of clamp 14 nonrestrainingly and forcefully seats its jaw members toward imprinted support 10, effecting a substantial fluid seal. Dam 18 is placed over clamp 14, and secured in its final position, as shown in FIG. 2.

On completion of any dental clinical procedures, the dental clamp forcep engages and separates clamp 14 jaw members. Clamp 14, support 10, and dam 18 are removed from the mouth. Residual adhesive 12 is wiped from the teeth or gingiva.

If donut 16 is desired to support and anchor clamp 14, rather than support 10, implementation is similar to that of support 10, with the following exceptions. Following application of adhesive 12 to the teeth or gingiva, softened donut 16 is placed over the occlusal surface of the anchor tooth, with any bulkier portions of donut 16 material oriented toward the buccal and lingual/palatal. The buccal and lingual/palatal portions are pulled gingivally, and molded to cover the tooth or gingiva, which is to support clamp 14, to approximately 2 mm in thickness. Simultaneously, the mesial and distal portions are worked away from the occlusal surfaces by pressing material into, the occlusal interproximal embrasures spaces. As such, the occlusal surface of the anchor tooth is relatively free of donut 16 material to facilitate clinical access, such as for endodontic access preparation. However, it is sometime desirable for donut 16 material to partly cover the occlusal surfaces of adjacent teeth, for strength and continuity of the material. Donut 16 is cooled somewhat, such as by a water spray, until the material begins to stiffen slightly, and regain some opacity. Clamp 14 is then applied over donut 16, similarly to support 10, as shown in FIG. 4.

Support 10 and donut 16 thus provide atraumatic anchorage and support for clamp 14. Support 10 and donut 16 are immediately reusable on the same site, without remolding, following reapplication of adhesive 12, lightly drying adhesive 12 until tacky, and pressing support 10 onto the same site. Support 10 and donut 16 are also reusable on a different site, following softening of the material.

It is sometimes assessed that support 10, without concurrent use of clamp 14 immediately over support 10, is most effective to anchor and support dam 18. This is most often applicable for anchoring dam 18 on anterior teeth, especially when dam 18 is slit to expose multiple teeth. Implementation of the device begins with softening one or more support 1I wafers, such as by heating. Softened support 10 is molded over the facial and lingual/palatal surfaces of the teeth or gingiva for which anchorage of the dental dam is desired. It is particularly useful to mold support 10 into retentive undercut areas about and between the teeth to enhance anchorage. It is also useful to mold extensions of support 10 along the adjacent gingiva into a shape capable of supporting dam 18 in a desirable configuration. Support 10 is hardened, such as by cooling with a water spray. Hardened support 10 is removed from the teeth and adjacent gingiva. Dam 18 is placed over the teeth and gingiva desired, at least a portion of which are the same teeth or gingiva over which support 10 was molded. Hardened support 10 is placed over dam 18, and over the same teeth or gingiva over which it was molded. Dam 18 is thus interposed between support 10, and the teeth or gingiva. Pressure is applied to engage support 10, and therefore dam 18, into retentive undercut areas about and between the teeth. Dam 18 is thus retentively anchored in the desired area of the mouth, such as shown in FIG. 5. On completion of any dental clinical procedures, support 10 is rapidly removable intact from the teeth, to release dam 18, by flexing the facial and lingual/palatal portions away from the teeth undercuts. Support 10 is also immediately reusable over the same site, or may be softened for remolding at another site. Support 10 thus provides atraumatic anchorage and extended support for dam 18.

It is sometimes assessed that donut 16, without concurrent use of clamp 14 immediately over donut 16, is most effective to provide precise barrier isolation about a specific area of the teeth. Donut 16 may isolate a surface area of a tooth while anchoring dam 18, as shown in FIG. 6.

Implementation of the device begins with softening a donut 16 wafer, such as by heating. Softened donut 16 is molded into retentive undercut areas about and between the teeth to enhance anchorage. It is particularly useful to precisely mold donut 16 as a perimeter barrier isolation circumscribing a specifically exposed work area of the teeth. As such, the surface areas of the teeth or gingiva under the barrier isolation are precisely isolated and protected from procedures upon the exposed work area. Donut 16 is hardened, such as by cooling with a water spray. Hardened donut 16 is removed from the teeth or gingiva. Dam 18 is placed over the same teeth or gingiva, dam 18 being trimmed such that it does not cover the exposed work area of the teeth. Hardened donut 16 is placed over dam 18, and over the same teeth or gingiva over which it was molded. Dam 18 is thus interposed between donut 16, and the teeth or gingiva. Pressure is applied to engage donut 16, and therefore dam 18, into retentive undercut areas about and between the teeth. Dam 18 is thus retentively anchored in the desired area of the mouth, a specific work area of the teeth is exposed, and the perimeter teeth or gingiva about the exposed work area are protected by precise barrier isolation. The donut 16 perimeter isolation area may be further sealed from the exposed work area, such as by flowing resin about the perimeter. On completion of any dental clinical procedures, donut 16 is rapidly removable intact from the teeth, to release dam 18, by flexing the facial and lingual/palatal portions away from the teeth undercuts. Donut 16 is also immediately reusable over the same site, or may be softened for remolding at another site. Donut 16 thus provides a moldable barrier for precise isolation around the teeth, capable of anchoring dam 18, and capable of rapid, intact removal without fracturing of donut 16.

Summary, Ramifications and Scope

Accordingly, the reader will see that the dam support of this invention provides a means for atraumatic anchorage and support for a dental dam or dental dam clamp. Such anchorage and support is thereby permitted even in areas where teeth have a low height of contour, or have no interproximal embrasures with adjacent teeth. The dam support facilitates substantial fluid sealing. The dam and clamp support has the additional advantages in that it can atraumatically support and anchor a clamp entirely on the gingiva, when necessary. This is particularly useful when extensive cavity preparation is required on the anchor tooth, such as for a crown. Furthermore, the dam support alone can be molded to anchor a dental dam to the teeth, support the configuration of the dam along the gingiva, provide specific isolation of tooth surface areas, and be rapidly removable without fracturing of the support material. As such, the dam support is reusable on the site without remolding.

Although the description above contains many specificities, these should not be construed as limiting the scope of the invention and process, but as merely providing illustrations of some of the presently preferred embodiments of this invention. For example, support 10 material may be additionally molded to form extensions away from clamp 14, to assist in retaining and configuring dam 18. Such molding may include formation, or use, of a cylinder of support 10 material for use as a custom intraoral dental dam frame, such as for supporting the configuration of dam 18, especially for slit dam procedures for general field isolation of more than one tooth. A dead soft wire frame along the length of the cylinder can enhance handling the material when softened.

As additional example, support 10 may be used to support clamp 14, or any other type of dental clamp, in applications other than dam 18 anchoring and contouring, to improve clamp stability and fluid sealing, and reduce clamp trauma.

Thus the scope of the invention should be determined by the appended claims and their legal equivalents, rather than by the examples given.

What is claimed is:

1. A method for supporting a dental clamp having opposing jaw members for engaging oral structures, such as teeth and gingiva, said jaw members biasable toward each other, said method comprising the steps of:

introducing a pliable mass of hardenable dental material onto portions of the teeth, portions of the gingiva, or portions of the teeth and gingiva, on which a dental clamp is desired;

molding said pliable mass of hardenable dental material to form a support of hardenable dental material;

restrainingly seating said jaw members partly into said support of hardenable dental material, such that said jaw members imprint said support of hardenable dental material, but do not completely penetrate said support of hardenable dental material, to form an imprinted support of hardenable dental material;

substantially hardening said imprinted support of hardenable dental material to form an imprinted support of substantially hardened dental material; and nonrestrainingly seating said jaw members partly into said imprinted support of substantially hardened dental material, such that jaw members are biased toward each other.

2. The method according to claim 1, wherein said hardenable dental material is a thermosetting material that melts or softens at a temperature less than 65° C., said material being solid at 38° C.

3. The method according to claim 2, wherein said thermosetting material is polycaprolactone.

4. The method according to claim 1, wherein an oral adhesive is interposed between said hardenable dental material and said oral structures.

5. The method according to claim 4, wherein said oral adhesive is water based acrylic emulsion.

6. A method for sealingly supporting a dental clamp having opposing jaw members for engaging oral structures, such as teeth and gingiva, said jaw members biasable toward each other, such that fluids are substantially sealed from flowing between said dental clamp and said oral structures, said method comprising the steps of:

introducing a pliable mass of hardenable dental material onto portions of the teeth, portions of the gingiva, or portions of the teeth and gingiva on which a dental clamp is desired;

molding said pliable mass of hardenable dental material to form a support of hardenable dental material;

restrainingly seating said jaw members partly into said support of hardenable dental material, such that said jaw members do not completely penetrate said support of hardenable dental material, and such that said support of hardenable dental material substantially seals fluids from flowing between said jaw members and said oral structures;

substantially hardening said support of hardenable dental material to form a support of substantially hardened dental material; and nonrestrainingly seating said jaw members partly into said support of substantially hardened dental material, such that jaw members are biased toward each other; and such that said support of substantially hardened dental material substantially seals fluids from flowing between said jaw members and said oral structures.

7. The method according to claim 6, wherein said hardenable dental material is a thermosetting material that melts or softens at a temperature less than 65° C., said material being solid at 38° C.

8. The method according to claim 7, wherein said thermosetting material is polycaprolactone.

9. The method according to claim 6, wherein an oral adhesive is interposed between said hardenable dental material and said oral structures.

10. The method according to claim 9, wherein said oral adhesive is water based acrylic emulsion.

11. A method for supporting a dental clamp on gingiva only, such as for use with teeth of insufficient structure to support said dental clamp, said dental clamp having opposing jaw members biasable toward each other, said method comprising the steps of:

introducing a pliable mass of hardenable dental material onto portions of the gingiva on which a dental clamp is desired;

molding said pliable mass of hardenable dental material to form a support of hardenable dental material;

restrainingly seating said jaw members partly into said support of hardenable dental material, such that said jaw members imprint said support of hardenable dental material, but do not completely penetrate said support of hardenable dental material, to form an imprinted support of hardenable dental material;

substantially hardening said imprinted support of hardenable dental material to form an imprinted support of substantially hardened dental material; and nonrestrainingly seating said jaw members partly into said imprinted support of substantially hardened dental material, such that jaw members are biased toward each other.

12. The method according to claim 11, wherein said hardenable dental material is a thermosetting material that melts or softens at a temperature less than 65° C., said material being solid at 38° C.

13. The method according to claim 12, wherein said thermosetting material is polycaprolactone.

14. The method according to claim 11, wherein an oral adhesive is interposed between said hardenable dental material and said gingiva.

15. The method according to claim 14, wherein said oral adhesive is water based acrylic emulsion.

16. A method for supporting a dental clamp having opposing jaw members for engaging oral structures, such as teeth and gingiva, said jaw members biasable toward each other, said method comprising the steps of:

applying an oral adhesive onto portions of the teeth, portions of the gingiva, or portions of the teeth and gingiva on which a dental clamp is desired;

introducing a pliable mass of hardenable dental material onto said oral adhesive;

molding said pliable mass of hardenable dental material to form a support of hardenable dental material;

restrainingly seating said jaw members partly into said support of hardenable dental material, such that said jaw members imprint said support of hardenable dental material, but do not completely penetrate said support of hardenable dental material, to form an imprinted support of hardenable dental material;

substantially hardening said imprinted support of hardenable dental material to form an imprinted support of substantially hardened dental material; and nonrestrainingly seating said jaw members partly into said imprinted support of substantially hardened dental material, such that jaw members are biased toward each other.

17. The method according to claim 16, wherein said hardenable dental material is a thermosetting material that melts or softens at a temperature less than 65° C., said material being solid at 38° C.

18. The method according to claim 17, wherein said thermosetting material is polycaprolactone.

19. The method according to claim 16, wherein said oral adhesive is a water based acrylic emulsion.

20. A method for making a dental dam anchor, and anchoring a dental dam with said dental dam anchor, comprising the steps of:
- heating an original unidentified mass of thermosetting material to a predetermined temperature range at which the thermosetting material becomes pliable, said thermosetting material is polycaprolactone;
- molding said mass of material while pliable on the teeth for which a dental dam anchor is desired;
- allowing said thermosetting material to cool and set, thereby forming a dental dam anchor;
- removing said dental dam anchor from said teeth;
- placing said dental dam on said teeth; and
- replacing said dental dam anchor on said dental dam, said dental dam remaining on said teeth, such that said dental dam is interposed between, and anchored by, said dental dam anchor and said teeth.

21. The method according to claim 20, wherein said polycaprolactone melts or softens at a temperature less than 65° C., said material being solid at 38° C.

22. A method for covering a perimeter area about an exposed work area of the teeth, comprising the steps of:
- heating an original unidentified mass of thermosetting material to a predetermined temperature range at which the thermosetting material becomes pliable, said thermosetting material is polycaprolactone;
- molding said mass of material while pliable to cover said perimeter area about said exposed work area;
- allowing said thermosetting material to cool and set, thereby covering said perimeter area about said exposed work area of the teeth.

23. The method according to claim 22, wherein said mass of thermosetting material has a thin layer of another material embedded into the external surface for convenience in handling.

24. The method according to claim 23, wherein said thin layer of another material is comprised of small particles.

* * * * *